United States Patent
Sergeevich et al.

(10) Patent No.: US 7,601,956 B2
(45) Date of Patent: Oct. 13, 2009

(54) METHOD FOR MEASURING DIFFRACTION PATTERNS FROM A TRANSMISSION ELECTRON MICROSCOPY TO DETERMINE CRYSTAL STRUCTURES AND A DEVICE THEREFOR

(76) Inventors: Avilov Anatoly Sergeevich, Litovsky Blvd h. 26 app. 84, Moscow (RU); Kuligin Kirill Vladimirovich, Shyolkovskoya shosse h. 77 app. 135, Moscow (RU)

( * ) Notice: Subject to any disclaimer, the term of this patent is extended or adjusted under 35 U.S.C. 154(b) by 415 days.

(21) Appl. No.: 10/570,336

(22) PCT Filed: Sep. 2, 2003

(86) PCT No.: PCT/EP03/09727
§ 371 (c)(1),
(2), (4) Date: Mar. 1, 2006

(87) PCT Pub. No.: WO2005/022582
PCT Pub. Date: Mar. 10, 2005

(65) Prior Publication Data
US 2007/0023659 A1    Feb. 1, 2007

(51) Int. Cl.
*H01J 37/04* (2006.01)
(52) U.S. Cl. .................. 250/311; 250/310
(58) Field of Classification Search .......... 250/311, 250/306, 307, 607
See application file for complete search history.

(56) References Cited

U.S. PATENT DOCUMENTS

| | | | |
|---|---|---|---|
| 3,849,647 A | 11/1974 | Koike et al. | |
| 4,697,080 A | 9/1987 | King | |
| 6,420,701 B1 | 7/2002 | Hashimoto | |
| 6,548,811 B1 * | 4/2003 | Nakamura et al. | 250/311 |
| 6,750,451 B2 * | 6/2004 | Koguchi et al. | 250/311 |
| 7,022,988 B2 * | 4/2006 | Taniguchi et al. | 250/311 |
| 2004/0000641 A1 * | 1/2004 | Taniguchi et al. | 250/311 |

OTHER PUBLICATIONS

Avalov, et al. "Scanning System for High-Energy Electron Diffractometry," *Journal of Applied Crystallography*, vol. 32, pp. 1033-1038, 1999.
Vincent, et al. "Double Conical Beam-Rocking System for Measurement of Integrated Electron Diffraction Intensities," *Ultramicroscopy*, vol. 53, pp. 271-282, 1994.
International Search Report dated May 13, 2004.

* cited by examiner

*Primary Examiner*—Nikita Wells
*Assistant Examiner*—Johnnie L Smith
(74) *Attorney, Agent, or Firm*—Knobbe, Martens Olson & Bear, LLP (57) ABSTRACT

A device and method which enable a transmission electron microscope to measure electron diffraction patterns of a sample very precisely are disclosed. The patterns are suitable for structure determination. The electron beam is precessed by means of deflector coils (6) in the transmission electron microscope before the sample (4), in combination with a similar precession of the electron diffraction pattern by means of deflector coils (9) situated after the sample. The electron diffraction pattern is scanned by means of deflector coils (9) situated after the sample.

23 Claims, 6 Drawing Sheets

METHOD FOR MEASURING DIFFRACTION PATTERNS FROM A TRANSMISSION ELECTRON MICROSCOPY TO DETERMINE CRYSTAL STRUCTURES AND A DEVICE THEREFOR

RELATED APPLICATIONS

This application is the U.S. National Phase under 35 U.S.C. 371 of International Application PCTEP2003/009727, filed Sep. 2, 2003.

BACKGROUND OF THE INVENTION

The macroscopic material world is formed by millions of crystals; every crystal at a microscopic level is formed by a cell having some symmetry for example hexagonal, trigonal, cubic etc, and having a specified quantity of atoms therein whose positions are defined. In order to understand the properties of matter is essential to know the crystal structure at atomic level; this requires atomic resolution structural studies by means of X-Rays, neutron or electron diffraction.

X-Ray diffraction is a technique which provides an average structure, usually of tens of thousands of particles. Newly synthesised materials are often in powder form and often present poor crystallinity for precise X-Ray structure determination.

Electron diffraction (ED) is much more sensitive than X-Ray diffraction, providing about a ten thousand fold enhancement in signal. Electron diffraction structure analysis of materials originally developed in the early 50's when diffraction intensities obtained from electron diffraction cameras were recorded on photographic films. Such films are good for reproducing contrast detail in transmission electron microscope (TEM) imaging, for example, however, they suffer from lack of dynamic range for recording intensity measurements of ED patterns. Therefore, they are not adequate for quantitative and precise structure analysis. Despite the limitations, however, many different structures of organic and inorganic substances have been determined up to now using ED and photographic films, albeit with low resolution. The studies contributed significantly to the fields of crystallography and crystal chemistry of solids.

A means for precise atomic structure analysis is linked to the increasing of reliability and precision in measuring ED intensity data. One important feature for accurate measurement of intensities in an ED pattern is ability of capture the high dynamic range of spot intensities, which can range between 1 and $10^6$ for the weakest and most intense spots respectively.

Another important issue when measuring ED data for resolving crystal structures is the speed at which intensities are measured. Radiation damage to most samples usually occurs for exposures lasting longer than a minute. Organic compounds are especially sensitive to radiation damage. Since the damage is irreversible and renders the crystal unusable for further diffraction studies, and crystals can take many weeks or months to prepare, any technique which reduces the exposure of the crystal to the beam would be advantageous.

In order to resolve successfully a structure from ED data, the intensities of the spots in an ED pattern need to be determined accurately with minimum beam damage to the sample. In practice, for structure analysis using ED, especially where light elements such as oxygen and hydrogen are detected in the cell, the precise measurement of about 50-100 reflections is sufficient to have an accurate picture of the crystal structure. This contrasts with X-Ray diffraction where several hundreds of reflections need to be measured.

For crystal structure determinations, which includes the determination of electrostatic potential and analysis of chemical bonding of crystals, the precision of measuring ED intensities should be high and preferably the same for all reflections. This is true also for the weakest intensities (i.e. those resulting from large diffraction angles), since they have a significant influence on the accurate determination of the light atoms in the structure.

Up to now analysis by ED has been performed, in most cases, using devices of the art whose primary purpose is to record electron diffraction patterns. These devices are known as electron diffraction cameras (EDC), and are characterised in that they do not have imaging lenses, they work at low-intermediate voltages (>100 kV) and have a beam size of the order of few microns. To obtain precise, quantitative analysis using an EDC requires the implementation of a pattern scanning system in front of a fixed counter mounted on the EDC (Avilov et al, *J. Appl. Cryst*. (1999), 32, 1033-1038)). With this technique the location of light atoms, such as hydrogen may be determined in the studied crystal structures, even when heavier atoms such as iron or aluminium are present. The electrostatic potential distribution and the electron density may be reconstructed in some cases. However, the scanning system has a lot of limitations. For example, it takes several hours to record with precision the reflections of an ED pattern. Therefore, only very few beam resistant samples can be precisely measured with this technique. Moreover, this type of scanning system is interfaced with EDCs whose beam size is generally too wide (micrometer range) for obtaining atom resolution detail.

ED patterns of crystals may also be measured using a transmission electron microscope (TEM). Structure analysis of crystals by ED in a TEM presents a lot of advantages over conventional X-Ray or neutron diffraction: the size of studied crystallites in TEM can be very small (even tens of Ångstroms), therefore individual phases in powders (nm size) can be examined.

Typically a TEM is interfaced to a slow scan charged-coupled device (CCD) camera or imaging plate for recording the ED patterns. However, problems with using a CCD camera or imaging plate for detection exist. For example, the dynamic range of the CCD camera is limited which leads to errors in measuring very intense or very weak intensities. Furthermore, continuous exposure of a CCD camera to high diffracted ED beam intensities can damage the CCD detector. Even, if in the near future those problems could be partially resolved in some commercial CCD cameras, the main problem of precision measurement (up to 1%) of all ED intensities—and specially the weakest ones—will remain. For instance, accuracy in intensity estimation for high angle (>5 Ångstroms$^{-1}$) reflections is very poor (up to 25% accuracy). Imaging plates for recording ED in a TEM can be constructed with the same area as the photographic films, and may be used together with photographic film in a TEM. Exposed plates may read with a laser beam; this system is claimed to have dynamic range over 100 times more than that of a commercial CCD camera. As with CCD cameras, the main problem of precision measurement (up to 1%) of all ED intensities—and specially the weakest ones—cannot be resolved with this technique.

The present invention relates to a method for obtaining an electron diffraction pattern from any conventional transmission electron microscope (TEM) which overcomes the problems of dynamic range, speed at which intensities are measured and sample deterioration in the beam, accounting for beam instability from which method and devices of the prior art all suffer. The invention is suitable for measuring with high precision electron diffraction intensities, correct them from dynamical contributions, and perform calculations to derive crystal structures at atomic resolution from nanometer size areas, or in the range afforded by the beam size the TEM.

SUMMARY OF THE INVENTION

One embodiment of the present invention is a method for measuring electron diffraction, ED patterns of a sample, said patterns suitable for structure determination therefrom using a transmission electron microscope, TEM, wherein the ED pattern is scanned by means of deflector coils in the TEM situated after the sample.

Another embodiment of the present invention is a method as described above wherein the electron beam is precessed by means of deflector coils in the TEM situated before the sample, in combination with a similar precession of the ED pattern by means of deflector coils situated after the sample.

Another embodiment of the present invention is a method as described above further comprising the steps before measurement of intensities of:
  a) exposing said sample to a low electron beam dose,
  b) fast recording an ED pattern using a charged-coupled device, CCD, camera, or, fast recording an ED pattern using a diffractometer in fast scan mode,
  c) blanking the beam,
  d) deducing one or more parameters from the ED pattern obtained in step b) to be used during the measurement of intensities,
  e) de-blanking the beam, and
  f) measuring precise intensities using the parameters determined in step d).

Another embodiment of the present invention is a method further comprising the steps before measurement of intensities of:
  a) exposing said sample to a low electron beam dose,
  b) fast recording an ED pattern using a charged-coupled device (CCD) camera or via a fast scanning by diffractometer,
  c) blanking the beam,
  d) deducing one or more parameters from the ED pattern obtained in step b) to be used during the measurement of intensities,
  e) de-blanking the beam, and
  f) measuring precise intensities using the parameters determined in step d).

Another embodiment of the present invention is a method as described above wherein parameters of step d) are one or more of:
  the number of spots or areas of the reciprocal space to be scanned,
  number of scanning steps,
  the step size.

Another embodiment of the present invention is a method as described above further comprising the steps of:
  a) comparing the intensity of a particular reflection measured during measurement of intensities with a reference reflection determined by the ED pattern captured by the diffractometer,
  b) determining sample degradation and/or beam stability from the comparison made in step a), and
  c) adjusting any parameters during measurement of intensities and/or adjusting the analysis after measurement of intensities Another embodiment of the present invention is a method as described above further comprising the steps of
  a) measuring the electron beam current during measurement of intensities using an insulated condenser diaphragm located in the path of beam, before the beam contacts the sample,
  b) determining beam stability by monitoring current in step a) over time, and
  c) adjusting any parameters during measurement of intensities and/or adjusting the analysis after measurement of intensities.

Another embodiment of the present invention is a method as described above wherein one or more Faraday cages are used to measure the reflections of the ED pattern during the measurement of intensities.

Another embodiment of the present invention is a method as described above further comprising the following steps:
  a) allowing charge from a Faraday cage to accumulate on a preamplifier which has a few femtoamperes of leakage current; the positive charge from transitive currents engaging said amplifier.
  b) discharging said Faraday cage during measurement of intensities by means of the electron beam,
  c) resolving the work of counter pulses using a managing two-threshold comparator acting from a quartz generator during a cycle of measurement.
  d) determining the charge on the Faraday cage from the output of said amplifier,
  e) determining the current of an electron beam from the number of pulses which have been recorded in the counter.

Another embodiment of the present invention is a method as described above wherein a combination of a scintillator and a photomultiplier is used to analyse the ED pattern during measurement of intensities.

Another embodiment of the present invention is a method as described above wherein a continuous dynode electron multiplier, CDEM, is used to analyse the ED pattern during measurement of intensities.

Another embodiment of the present invention is a device suitable for interfacing with a TEM, enabling said TEM to measure ED patterns of a sample, said patterns suitable for structure determination, comprising a scan generator and a precession signal generator.

Another embodiment of the present invention is a device as described above further comprising an inverter and adapter connected to the output of the signal precession generator.

Another embodiment of the present invention is a device as described above further comprising a CCD camera and/or a diffractometer.

Another embodiment of the present invention is a device as described above further comprising an insulated condenser diaphragm located in the path of beam, before the beam contacts the sample.

Another embodiment of the present invention is a device as described above further comprising one or more Faraday cages, a combination of a scintillator and a photomultiplier, and/or a CDEM, each having an analogue-to-digital converting means.

Another embodiment of the present invention is a device as described above further comprising a computer having a computer readable storage means which interfaces to one or more of the above devices.

Another embodiment of the present invention is a device as described above further comprising a mounting enabling one or more Faraday cages, a combination of a scintillator and a photomultiplier, and/or a CDEM to be fitted at the bottom of the TEM column, and/or in the 35 mm camera port, and/or in any available port.

Another embodiment of the present invention is a device as described above further comprising a Faraday cage preamplifier that has a current leakage of between 1 and 50 femtoamperes.

Another embodiment of the present invention is a use of a device as described above for measuring ED patterns of a sample, said patterns suitable for structure determination therefrom using a transmission electron microscope.

Another embodiment of the present invention is a method for determining sample degradation in a sample undergoing diffraction studies comprising comparing the intensity of a particular reflection measured during measurement of intensities with a reference reflection determined by the ED pattern captured by the CCD camera or a diffractometer.

Another embodiment of the present invention is a TEM capable of performing a method as described above.

Another embodiment of the present invention is a TEM comprising a device as described above.

Another embodiment of the present invention is an ED pattern measured according to a method as described above, or a device as described above, or a TEM as described above.

The present invention is a method and device that can interface to any TEM of the art or future TEM that enables said TEM to rapidly and precisely measure all ED reflections in any diffraction pattern of any zone axis, while minimizing the damage to radiation sensitive and non-radiation sensitive samples.

The method and interface implement a scanning protocol in the TEM whereby the electron beam is deflected by means of deflector coils in the TEM which are situated after the sample.

The method and interface optionally implement a precession of the electron beam by means of deflector coils in the TEM which are situated before the sample in combination with a similar precession of the beam below the sample.

The method and interface comprise use of any CCD camera (such as a domestic video camera, web camera, a security camera, specialist CCD camera) which records an ED pattern resulting from a brief exposure of the sample to the beam, after which the beam is blanked. The data captured in this low dose mode by the CCD camera is used to preset parameters such as area to be scanned, precession mode, step size of scanning.

The method and interface may also use a diffractometer in place of a CCD camera. The device which is used to measure intensities is called diffractometer.

The method and interface comprise use of a Faraday cage, a combination of a scintillator and a photomultiplier, or continuous dynode electron multiplier (CDEM) to record the ED pattern in order to obtain a crystal structure.

The invention relates to a combination or one or more of the above features.

DETAILED DESCRIPTION OF THE INVENTION

One embodiment of the present invention is a method for measuring electron diffraction (ED) patterns of a sample from a transmission electron microscope (TEM) wherein the ED pattern is scanned by means of deflector coils situated after the sample. The diffraction pattern is moved in a step-by-step scanning mode across a motionless (fixed) detector. The invention represents an improvement on the methods known in the art for scanning, such as, for example, that disclosed by Avilov et al, 1999 in relation to an EDC.

A sample according to the invention, is any substance susceptible to crystallographic study. Examples include nanocrystals, powders.

Another embodiment of the present invention is a method as disclosed herein wherein the electron beam is precessed by means of beam tilt coils in the TEM which are situated before the sample in combination with a similar precession of the ED pattern via deflection coil below the sample (Vincent and Midgley 1998). The measurement of ED intensities in a precession mode allows all ED intensities to be recorded under reduced influence from dynamical diffraction and double scattering contributions, so permitting structure analysis of improved precision. Methods for implementing a precession mode in a TEM are known in the art. By precessing an incident beam at a constant angle around a zone axis in combination with a similar precession of the ED pattern below the specimen (Vincent and Midgley 1998), the equivalent mechanism of the precession of the specimen is obtained.

Another embodiment of the present invention is a method for measuring ED patterns from a TEM comprising a combination of the aforementioned scanning mode and precession mode. In this embodiment the reflections are swept successively through the Ewald sphere and the resulting integrated intensities are recorded by the system together with the angle of precession and the deflection/scanning of all the ED spots. An aspect of the invention calculates the crystal structure resulting from said integrated intensities.

The combination of the precession and scanning methods reduces the sensitivity of ED intensities to crystal thickness, reduces the effect of Ewald sphere curvature and can also reduce a lot of multiple beam dynamical effects contribution to the reflections. This way all ED reflections are much more kinematical in character e.g. a quality of structure analysis can be greatly improved.

Another embodiment of the invention is a method for measuring ED patterns from a TEM, wherein any CCD camera is used to record an ED pattern resulting from a brief exposure of the sample to the beam, after which the beam is blanked. The ED pattern captured by the CCD camera is used to preset parameters such as the step size in pixels, area to be scanned, precession mode activation which are used during the measurement of intensities with the diffractometer. By exposing the sample to the beam for a short period and subsequently blanking-off (shutting off) the beam, the sample is exposed to the damage of the electron beam for a very short period. The ED pattern captured by the CCD camera is not used to calculate the crystal structure, but is used to preset parameters for use during the measurement of intensities. The exposure may last for no longer than 1 ms, 2 ms, 10 ms, 100 ms, 200 ms, 1 s, 2 s, 5 s, 10 s, 20 s, 25 s, 30 s, 40 s, 50 s, or 60 s.

The term "measurement of intensities" as used herein, means the acquisition of an ED pattern which is transformable into structural data. Such data is measured by, for example, one or more Faraday cages, a combination of a scintillator and a photomultiplier, or a CDEM. By contrast, measurements made by the aforementioned CCD camera are not usually taken during the measurement of intensities; measurements made by the CCD camera are usually taken prior to the measurement of intensities and are usually used to set parameters used during the measurement of intensities.

It is an aspect of the invention that during the brief exposure of the sample to the beam and capture of the ED pattern by the CCD camera, the electron beam is precessed and/or the ED pattern scanned according to a method of the invention as described herein.

An example of a parameter that may be set using the ED pattern captured by the CCD camera is one or several predetermined sections of reciprocal space of the ED pattern that is recorded during the measurement of intensities. To record a whole ED pattern would be very time consuming and would lead to deterioration of the crystal. By using ED pattern captured by the CCD camera, the TEM can be set up to record the whole ED pattern, or a pre-selected number of spots or areas of the reciprocal space, while minimizing beam damage to the sample. This way a complete set of intensities may be obtained from the same crystal and a complete set of structure factors with statistical precision of 1-2% for complete structure determination.

Other examples of parameters that can be set using the ED pattern captured by the CCD camera are the number of scanning steps and the step size (in pixels). The information gathered by the CCD camera allows the user to choose these prior to the measurement of intensities, which constitutes a clear advantage in comparison with systems where the number of pixels is predefined. That way, structural aspects like superstructure reflections, satellite commensurate-incommensurate reflections or diffusion backgrounds can be refined in very precise way and separately to main structure reflections.

The ED pattern captured by a diffractometer may also be used to monitor the stability of the measurement during the measurement of intensities. The stability of the measurement can be confirmed by frequently comparing the intensity of a particular reflection with the reference reflection determined by the ED pattern captured by the diffractometer. Since radiation damage alters drastically all intensities of ED pattern, radiation damage that alters the sample can be immediately detected. Furthermore, the effects of beam instability also affects the intensities of an ED pattern, therefore beam instability may be detected also. Thus, any beam instability or radiation damage can be incorporated into the structure calculation, so leading to structures of better precision. Alternatively, any beam instability may be detected during measurement of intensities and used to change parameters during the measurement of intensities.

In another embodiment of the present invention, a method of using a CCD camera to record an ED pattern resulting from a brief exposure of the sample to the beam, is used in a TEM that does not necessary apply the scanning and/or precession protocols disclosed herein. Thus, the use of a CCD camera to record an ED pattern resulting from a brief exposure of the sample to the beam method can be applied to any device or any method presently used or used in the future for obtaining an ED pattern in order to preset parameters used during the measurement of intensities.

In another embodiment of the invention, a method of using a CCD camera to record an ED pattern resulting from a brief exposure of the sample to the beam is used in combination the scanning protocol and/or the precession protocol disclosed above. In combination with a scanning protocol and/or the precession protocol, the areas of reciprocal space or numbers of spots may be pre-selected for scanning of the ED pattern over the fixed measuring unit, and also the number of scanning steps, the step size of scanning and/or precession mode activation.

Another embodiment of the invention is a method for measuring ED patterns from a TEM, wherein an isolated condenser diaphragm C2 is used to monitor the beam current during the measurement of intensities. The measurements obtained from the isolated condenser diaphragm is used to monitor intensity drift of the primary beam, and to make adjustments to the resulting ED pattern or interpretation thereof. Alternatively, any beam instability may be detected during measurement of intensities and used to change parameters during the measurement of intensities. Since drift of the primary beam leads to inaccuracies of the resulting ED pattern, a method which monitors the primary beams leads to a more accurate ED pattern and hence structure. The isolated condenser diaphragm may be C1 or C2 aperture (located before the sample). Another aspect of the invention is a special diaphragm holder suitable for placing the isolated condensor diaphragm in the beam. The method of monitoring the primary beam current using an isolated condenser diaphragm may be used in combination with any of the methods disclosed herein.

Another embodiment of the present invention is a method to scan the ED pattern in x and y direction or in spiral mode following the symmetry of the ED pattern.

Another embodiment of the present invention is a method for measuring ED patterns from a TEM, wherein one or more Faraday cages are used to detect ED during the measurement of intensities. In another embodiment, a combination of a scintillator and a photomultiplier is used to detect ED during the measurement of intensities. In another embodiment, a continuous dynode electron multiplier (CDEM) is used to detect ED during the measurement of intensities. In another embodiment, a combination of one or more of the aforementioned detectors is used to detect ED during the measurement of intensities. The dynamic range ($10^8$) of one or more of these devices is sufficient for obtaining the desired precision.

According to one aspect of the invention, the measurement of intensity using a Faraday cage comprises the following steps:

1) Charge from a Faraday cage accumulates on a preamplifier which has a few femtoamperes of leakage current; the positive charge from transitive currents engages said amplifier.

2) During measurement, the electron beam discharges said Faraday cage,

3) A managing two-threshold comparator resolves work of counter pulses acting from a quartz generator during a cycle of measurement.

4) The voltage output of said amplifier is proportional to the charge on the Faraday cage, and is derivative of a voltage on time is proportional to a current of an electron beam.

5) By changing with the help of a computer values of thresholds of said comparator, which determine the beginning and end of a cycle of measurement, it is possible to reduce or increase time of measurement in a point of a DP.

6) The number of pulses which have been recorded in the counter at end of measurement is inversely proportional to a current of an electron beam.

The inventors have found that the method advantageously provides a very high dynamic range, capable of detecting current differences between 1 and 10 exp 7.

The leakage current may be in the range of 0.001 to 0.01, 0.01 to 0.1, 0.1 to 1, 1 to 5, 1 to 10, 1 to 20, 1 to 50, 1 to 70, 1 to 100, 1 to 200, 1 to 300, 1 to 400, 1 to 500, 1 to 600, 1 to 700, 1 to 800, 1 to 900 femtoamperes.

In one aspect of the invention, the method is used to make one dimensional scans to measure, for example, the intensity versus radius in ring patterns from polycrystalline samples or it may be used to make two-dimensional x-y scans with intensities of small single crystals (spot ED patterns). The time taken to record intensity for a linear or two-dimensional scan increases with the angular resolution and the accuracy of the measurement that is desired. The reflection intensities can be measured as the sums of the intensities recorded at each point of the scanned profile. The computer of the system can carry out the measurement both in accumulation mode (to achieve the required statistical accuracy) or the constant—time mode.

Another embodiment of the present is one or more devices that can be interfaced to a TEM that enables said TEM to measure ED patterns from a sample. In one aspect of the invention, said device is capable of connecting to a TEM which is not normally equipped for measuring ED patterns. For example, a TEM might possess a set of deflection coils located before and after the sample, but the TEM might not be equipped with a set of amplifiers to drive the coils or with a device to generate precession or scanning signals. One or more devices according to the invention provides functionality to the TEM, enabling said TEM to perform a method of the invention. In another aspect of the invention, said device is capable of connecting to a TEM which is partially equipped for measuring ED patterns. For example, a TEM might possess a set of deflection coils located before and after the sample, and with a set of amplifiers to drive the coils, but have no means to generate precession or scanning signals according to the invention. One or more devices according to the invention provides functionality to TEM, enabling said TEM to perform a method of the invention.

In one aspect of the invention, a device(s) comprises components which enable the TEM to perform one or more of the aforementioned methods separately or in combination. For example, said device(s) enables the TEM to perform the scanning protocol and/or precession protocol and/or record an ED pattern resulting from a brief exposure of the sample to the beam and/or perform the measurement of intensities of ED patterns using one or more Faraday cages, a combination of a scintillator and a photomultiplier, or a CDEM.

The device(s) and method according to the present invention enables any TEM to be adapted to measure atomic structures of materials. Since the electron beam in a TEM is about $10^4$ times more intense than X-ray radiation, results from ED according to the invention are comparable in intensity to those obtained using Synchrotron radiation, without the expenditure or inconvenience associate with obtaining or being allocated time on a Synchrotron.

Examples of devices include, but are not limited to those listed below. One or more of said devices may be incorporated in a single device.

a scan generator, to control the coils that scan ED pattern according to a method invention, a precession signal generator to control the coils that precess the electron beam according to a method of the invention, an inverter and adapter to rotate the phase of the precession signal generator. The signal from said device combines with the signal of the scan generator so that the scanning of the ED pattern is countered during precession of the beam (see FIG. 3), a universal interface which adjusts the output of the precession signal generator and/or the scan generator, suitable for input into the coils of the TEM.

a rack of amplifiers suitable for driving TEM coils, should suitable amplifiers be absent from the TEM. Said amplifiers may be integrated into the interface, a CCD camera such as a low resolution camera, a web cam, a video camera, or a high-resolution camera, an analogue-to-digital means which connects to the CCD camera, a diffractometer such as a retractable Faraday cage suitable for insertion into the 35 mm camera port, an analogue-to-digital conversion means with or without a pre-amplifier which connects to the diffractometer, an isolated condenser diaphragm on a diaphragm holder, a detector for the measurement of intensities such as one or more Faraday cages, a combination of a scintillator and a photomultiplier, or a CDEM, an adapter for fitting the detector used to measure intensities to any TEM, an analogue-to-digital conversion means with or without a pre-amplifier which connects to the detector used to measure intensities, a computer having a computer readable storage means which interfaces to one or more of the above devices, and a computer program stored on a computer readable means for controlling scan generator and precession signal generator, and/or recording and analysing CCD/diffractometer data, and/or recording and analysing ED pattern collected during measurement of intensities.

Figure 2:
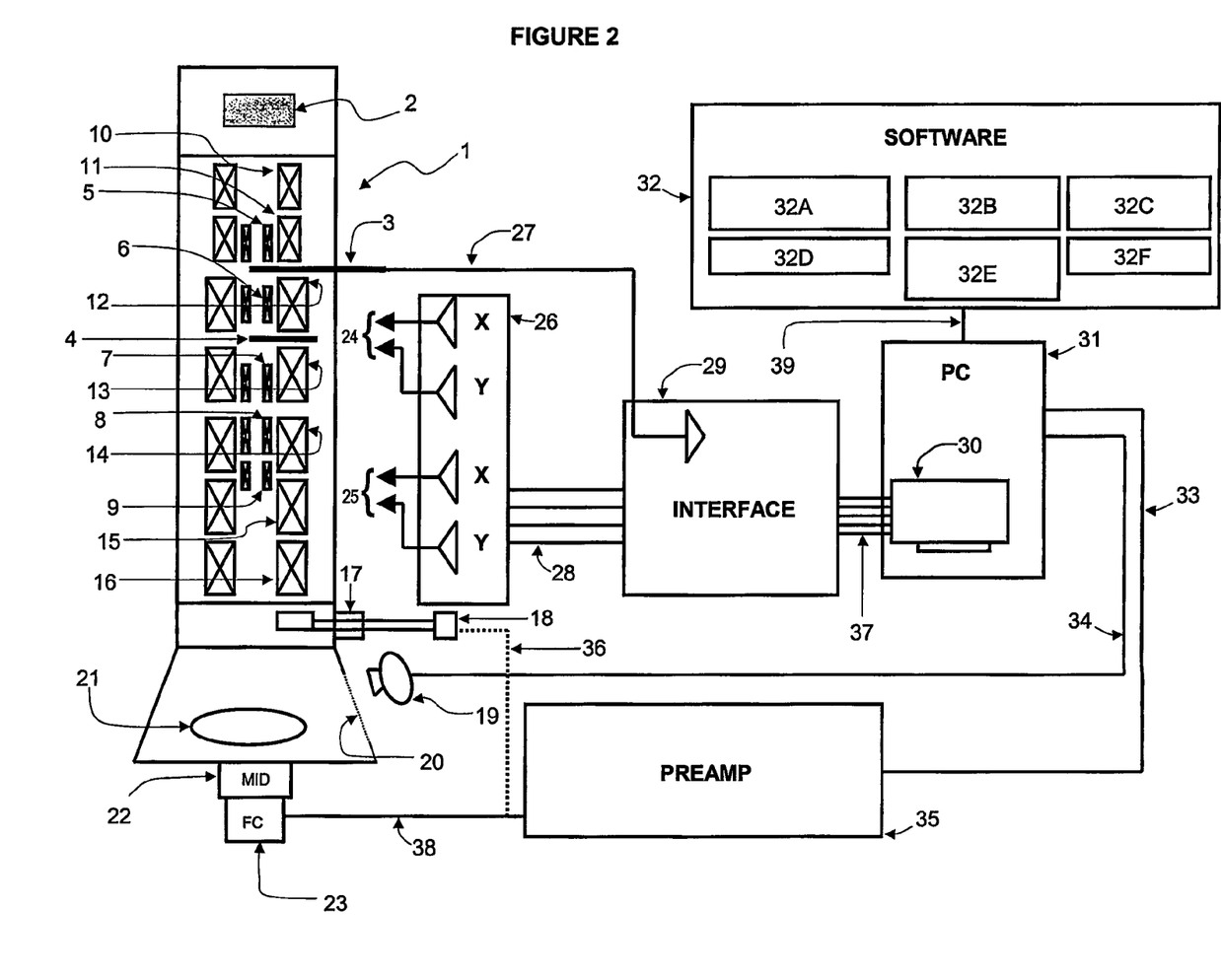

An example of a configuration of the components disclosed above is given in FIG. 2. In FIG. 2, all the devices mentioned above are shown, however, some may be absent, depending on which devices are already present in the TEM. Note also that either the diffractometer, or the CCD camera may be present, both may be present or none may be present. Note also that isolated condenser diaphragm may be absent or present. The associated circuitry may be absent or present as determined by the skilled person and the circuitry available.

Connections between the above mentioned devices may be direct or indirect; additional components may be inserted between device as known as understood by the skilled artisan.

According to one aspect of the invention, the diffractometer can be mounted in any available port of any TEM or inside the column of the TEM. Examples of ports include example on-axis, or on the 35 mm port. The flexibility of mounting permits compatibility with any TEM having other devices already mounted or that may be mounted in the future. According to another aspect of the invention CCD camera may be positioned in a front of a window, on the 35 mm port or any port of the TEM suitable for capturing an image of an ED pattern.

In one aspect of the invention the CCD camera or diffractometer connects to the computer directly or via an analogue to digital converter.

Another aspect is a mounting for the detector for the measurement of intensities, the design of which enables the user to obtain high precision ED pattern intensities, even if the position below the projection chamber is unavailable because of possible existence of CCD cameras or energy filters. Thus, one or more Faraday cages, a combination of a scintillator and a photomultiplier, or a CDEM can be fitted at the bottom of the TEM column or in the 35 mm camera port. The flexibility of the mounting even enables a detector to be directly fitted to an EELS spectrometer (e.g. of Wien type), allowing an energy filtered diffraction pattern to be obtained. The advantage of precise intensity measurement of such filtered ED pattern is that one can not only has access to the crystal structure and the chemical bonding, but also to physical parameters like diamagnetic susceptibility, polarisability, and even information regarding Energy gaps in some structures.

Using a method or device of the invention, all types of diffraction patterns can be measured (e.g. ring type from polycrystalline samples, spot diffraction patterns from any single crystal zone axis orientation, texture patterns). The inventors have found that the precision in measurement of ED intensities is adjustable up to 1% in intensity or better for both high intense and low intense reflections, so allowing a very precise structure determination that enables even hydrogen atoms to be revealed in the structure and/or the type of crystal bonding.

According to one aspect of the invention, the computer controls the scanning and/or precession protocols and records the ED patterns from both the CCD camera or diffractometer, and the Faraday cage(s), a combination of a scintillator and a photomultiplier, and/or CDEM.

One aspect of the invention is an algorithm that allows data obtained from the CCD camera or diffractometer to be used to present parameters used in the measurement of intensities.

All ED intensity data that are measured by the system can be automatically controlled via computer, which after performing various mathematical operations for crystal structure refinement will automatically propose to the user one (or several) crystallographic models for the studied sample.

One aspect of the invention is an algorithm that transforms the raw data, enabling the calculation and refining of cell parameters by least squares, calculate Patterson and Fourier maps for structural model refinement. The algorithm also uses direct methods (including maximum entropy methodology) to find the atomic locations into the structure (including light atoms such as H) and reconstruct the electrostatic potential using both Fourier methods and atomic or ionic kappa models to reveal the nature of crystal bonding. The software of the system can also read ED patterns recorded with CCD cameras, diffractometers or imaging plates, therefore it can be easily interfaced with those systems to constitute a complete metrology system of measuring ED intensities and refining crystal structures.

Another aspect of the present invention is a TEM comprising one or more of the devices disclosed herein. Another aspect of the present invention is a TEM capable of performing one or more of the methods of the present invention. Another aspect of the present invention is a TEM comprising one or more of the devices disclosed herein, capable of performing one or more of the methods of the present invention.

FIGURES

Figure 1:
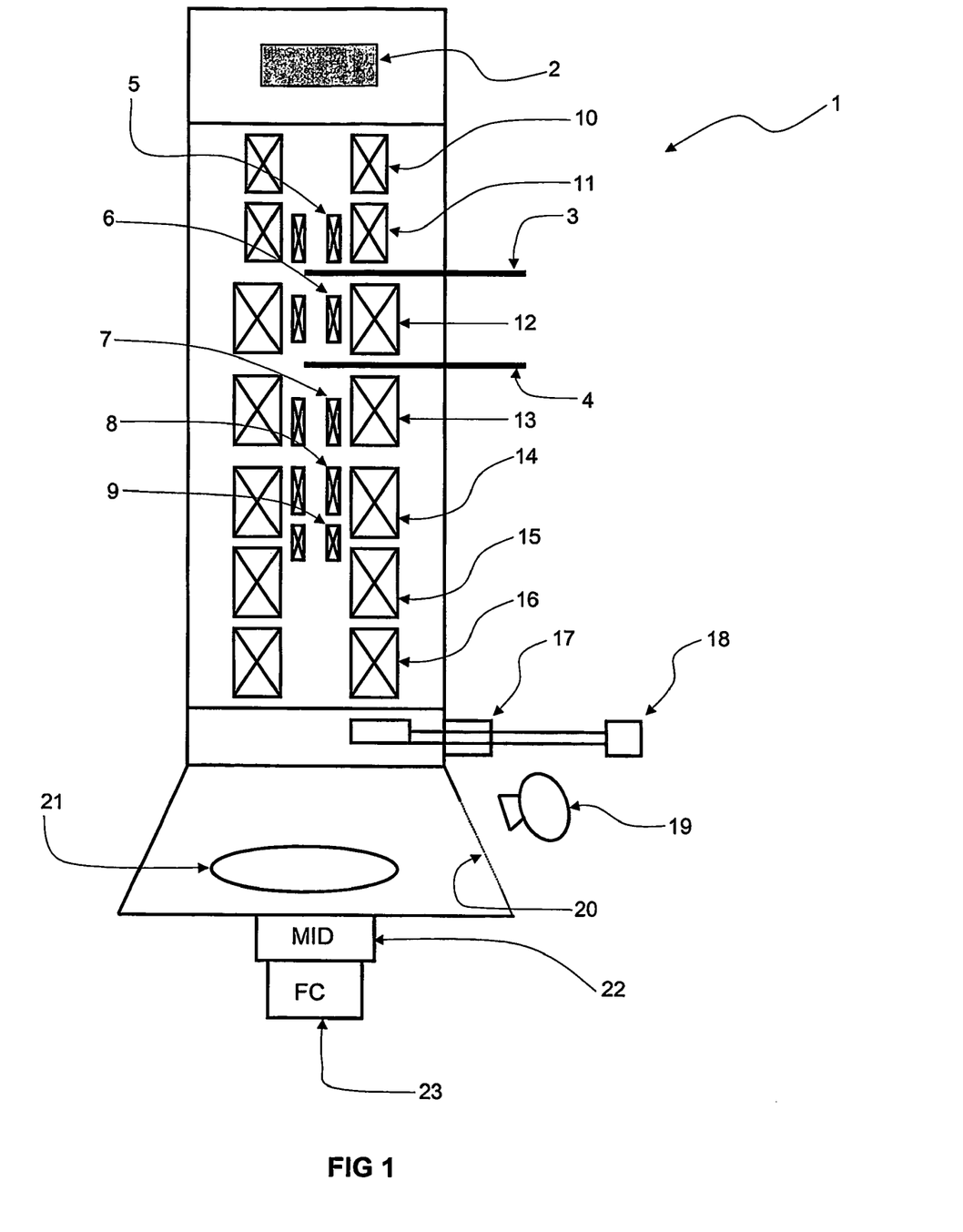

FIG. 1 represents a possible arrangement of one or more devices of the invention and a TEM. A TEM 1 comprises a gun 2, which emits electrons which pass proximal to a series of coils or lenses (5 to 16) which focus and deflect the beam. Indicated in FIG. 1 is a cross-section through the lens; since the lenses are circular coils, the view depicts two cross-sections for each coil and labeled are the right hand cross-sections for each coil. According to the example shown here, the coils are condenser stigmator coils (CSC) 5, deflection and beam tilt coils (DBTC) 6, objective stigmator and alignment coils 7, diffraction stigmator coils (DSC) 8, diffraction and intermediate alignment coils (DIAC) 9, a first condenser 10, a second condenser 11, the upper part of the objective lens 12, the lower part of the objective lens 13, the diffraction lens 14, the intermediate lens 15, the projective lens 16. The CSC 5 is situated in the second condenser coil 11. The DBTC 6 contains a rotation alignment coil, a deflection coil and a beam tilt coil; it is situated in the upper part of the objective lens 12. The DIAC 9 is the last coil used for scanning the diffraction image onto the diffractometer according to one aspect of the invention. The TEM may also comprise a 35 mm port 17 through which a diffractometer or a CCD camera of the invention may be inserted as described above. In FIG. 1, a diffractometer with a retractable Faraday cage 18 is inserted in the 35 mm port 17. The TEM may also comprise a window in the projection chamber 20. In FIG. 1, a CCD camera of the invention 19 is positioned such that it takes a diffraction image through the window of the projection chamber 20. The TEM may also comprise a fluorescent screen 21. Shown in FIG. 1 is a mechanical interface, MID, 22 of the invention to which a Faraday cage, FC, 23 may be coupled. The FC 23 may be used to measure intensities. Another aspect of the invention is an isolated condenser diaphragm and holder 3; this special diaphragm holder with isolated condenser diaphragm is used to measure the primary beam stability of the microscope and may be inserted into the C2 beam aperture. Shown also in the figure is the specimen 4.

FIG. 2 represents a possible arrangement of a device of the invention, together with a TEM. Arrows 1 to 23 are the same as for FIG. 1. A TEM according to the invention may also comprise an electronic rack of amplifiers 26 which connects to one or more lenses, for example, the DBTC 24 (for controlling precession) and to the DIAC 25 (for controlling scanning and descanning of the diffraction image). Should the TEM not already comprise such a rack of amplifiers, said rack of amplifiers 26 may a device of the invention. An interface 29, is a device that adjusts the output of the precession signal generator and/or the scan generator circuits 30 such that they are suitable for input into the coils of the TEM. The TEM may be equipped with an electronic rack of amplifiers 26, in which case the interface 29 provides a signal suitable for input into said amplifiers. Alternatively, the electronic rack of amplifiers 26 may be absent from the TEM, in which case said electronic rack of amplifiers 26 may be a device of the invention or integrated into the interface. The electronic rack of amplifiers 26 may be connected to the interface 29 via one or more cables 28. The interface 29 may also be connected via one or more cables 27 to the optional isolated condenser diaphragm 3, to record primary beam current. The interface 29, may be connected via one or more cables 37, to a printed circuit board 30 that contains components connected and configured to generate scan and precession signals. The circuit board is connected to a computer 31. The circuit board 30 may be of a type that can slot directly into a computer as is shown in the figure e.g. a PCI board, or it may connect to a computer via a port on a computer (e.g. serial, parallel, SCSI, USB, Firewire etc). In the figure, the CCD camera 19, connects to the computer via one or more cables 34; the connection may be any such as, for example, serial, parallel, SCSI, USB, Firewire etc. The Faraday cage used to measure intensities 23, is connected to a high precision, high dynamic range, high speed pre-amplifier 35, said preamplifier amplifying the output of the Faraday cage 23 so enabling measurement of the intensity of the ED pattern. Optionally connected to the preamplifier 35 via one or more cables 36 is the Faraday cage 18. The output of the preamplifier 35 is connected to the computer 31 via one or more cables 33. The preamplifier may also comprise an analogue to digital (A/D) converter. The output of the amplifier in the example shown is digital and may be configured to connect directly to a computer port, e.g. serial, parallel, SCSI, USB, Firewire. The personal computer 32 has a computer readable medium, that contains an image of software suitable for performing as necessary one or more of the following tasks: setting scan generator parameters 32A, setting precession signal parameters 32B, recording and analyzing a data obtained via CCD/diffractometer 32C, recording an ED pattern obtained via a Faraday cage 32D, analysing the diffraction image(s) 32E.

Figure 3:
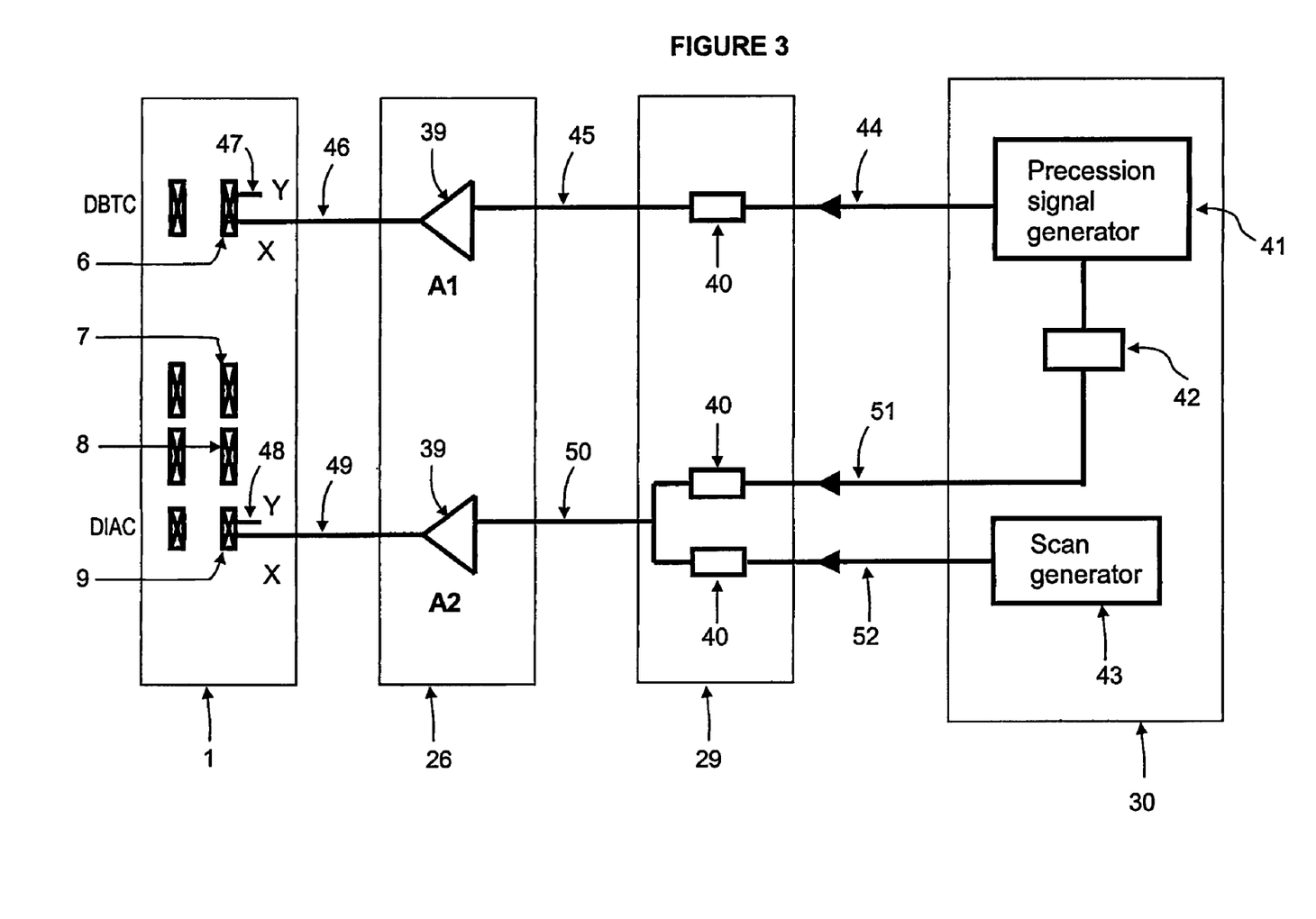

FIG. 3 represents a detail of the invention depicting a TEM 1, connected to an electronic rack of amplifiers 26, which in turn is connected to an interface 29, which in turn is connected to a printed circuit board 30. The TEM comprises at least DBTC 6, OSDAC 7, DSC 8 and DIAC 9. In this illustration, a device of the invention controls the DBTC 6 and the DIAC 9; furthermore, only illustrated are components for processing the beam and scanning the diffraction image in the X-direction; those components for precession the beam and scanning the diffraction image in the Y-direction, connected to the TEM via 47 and 48, are not shown for clarity, but would be similar or identical. Connected to the DBTC 6 and the DIAC 9 via one or more cables 46 and 49 respectively is an electronic rack 26 comprising amplifiers 39. Some TEMs already have amplifiers, in which case the electronic rack 26 is part of the TEM; in some TEMs the amplifiers are absent, in which case, the electronic rack 26 may be a device of the invention or integrated into the interface 29. Connected to the amplifiers 39 via one or more cables 45 and 50, is an interface 29 comprising resistors 40. The resistors 40 allow the signals from the precession signal generator 41 and the scan generator 43 to connect and be compatible with the amplifiers 39 of the electronic rack 26. Connected to the interface 29, via one or more cables 44, 51 and 52, is a printed circuit board 30, comprising a precession signal generator 41, a scan generator 43, and an inverter and adapter 42. The precession signal generator 41 provides a signal to scan the electron beam at a constant angle for the precession technique. The signal may be sinusoidal or square. The scan generator provides a sawtooth (or spiral) signal enabling a scan in the X and Y direction of the diffraction image onto the Faraday cage. The precession signal generator 41 is connected to an inverter and adapter 42 that rotates the phase of the signal generated by the precession signal generator 41. The signal from inverter and adapter 42 is supplied to the DIACs 9 along with the signals from the scan generator 43; the effect of the combination of signals to the DIACs is a precise countering of the motion of the diffraction image when the precession technique is used.

Figure 4:
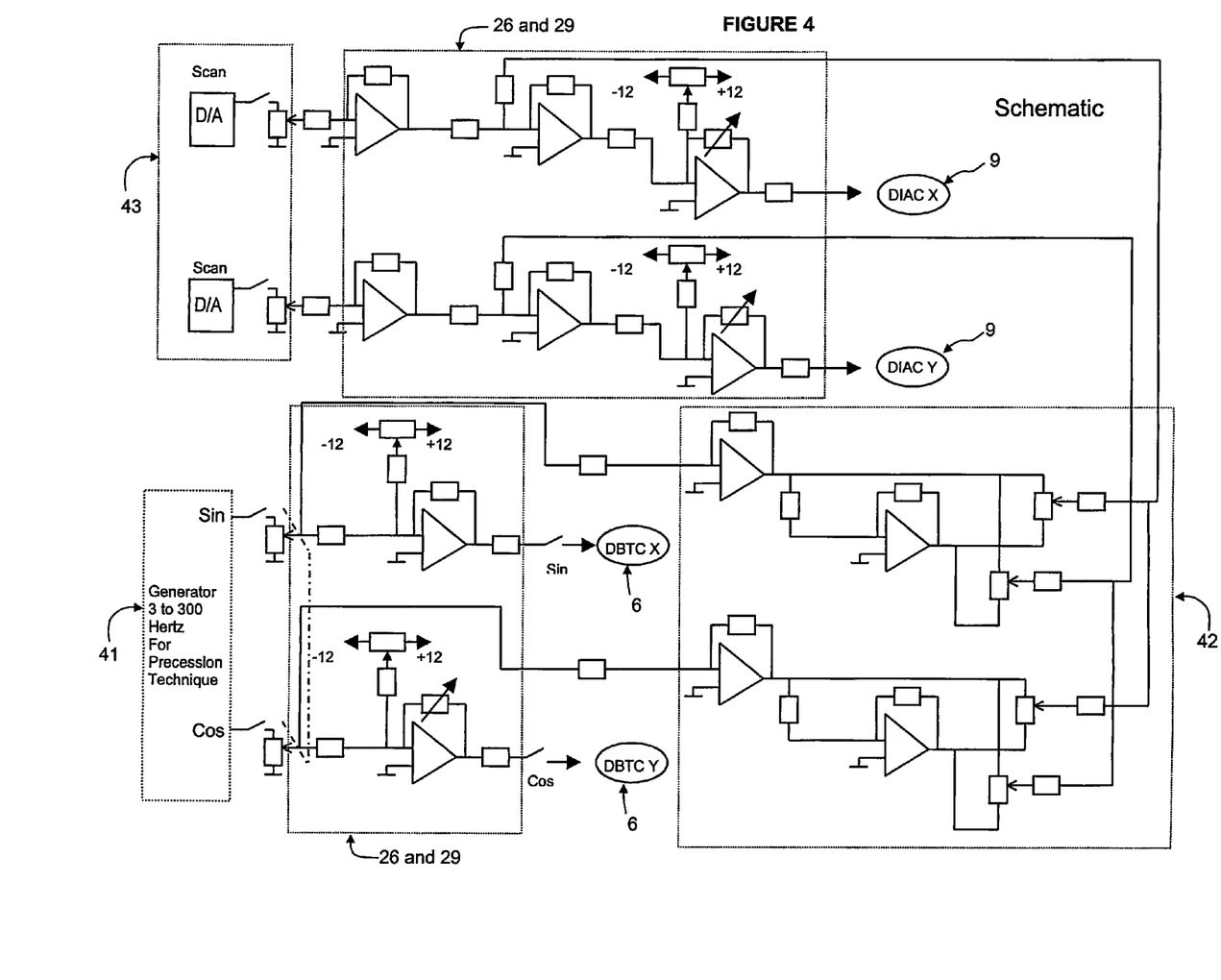

FIG. 4. Illustrates a detailed embodiment of the invention. The electrical symbols therein are known and understood by the skilled artisan. For clarity, the circuitry has been divided into sections, each of which has been labeled to correspond with a device or TEM of a previous figure; the divisions should not be taken as absolute since the skilled artisan may find it necessary to insert or remove components according to the type TEM and other operating conditions. A scan generator 43, comprising two digital to analogue converters (D/A) provides X and Y signals for scanning the diffraction image in the X and Y directions or in spiral to the TEM DIAC X and Y 9. The electronic rack of amplifiers and interface 26 and 29, situated between 43 and 9 perform any necessary electrical conversions and alignment signals. A precession signal generator 41, provides X and Y signals for precessing the beam in the X and Y directions to the TEM BDTC X and Y 6. The signals generated from 41 may be sinusoidal, cosinusoidal or square and be between 3 to 3000 Hz The electronic rack of amplifiers and interface 26 and 29, situated between 41 and 6 perform any necessary electrical conversions. The inverter and adapter 42 rotates the phase of the signal generated by the precession signal generator 41. The signal from inverter and adapter 42 is supplied to the DIACs 9 along with the signals from the scan generator 43; the effect of the combination of signals to the DIACs is a precise countering of the motion of the diffraction image when the precession technique is used.

Figure 5:
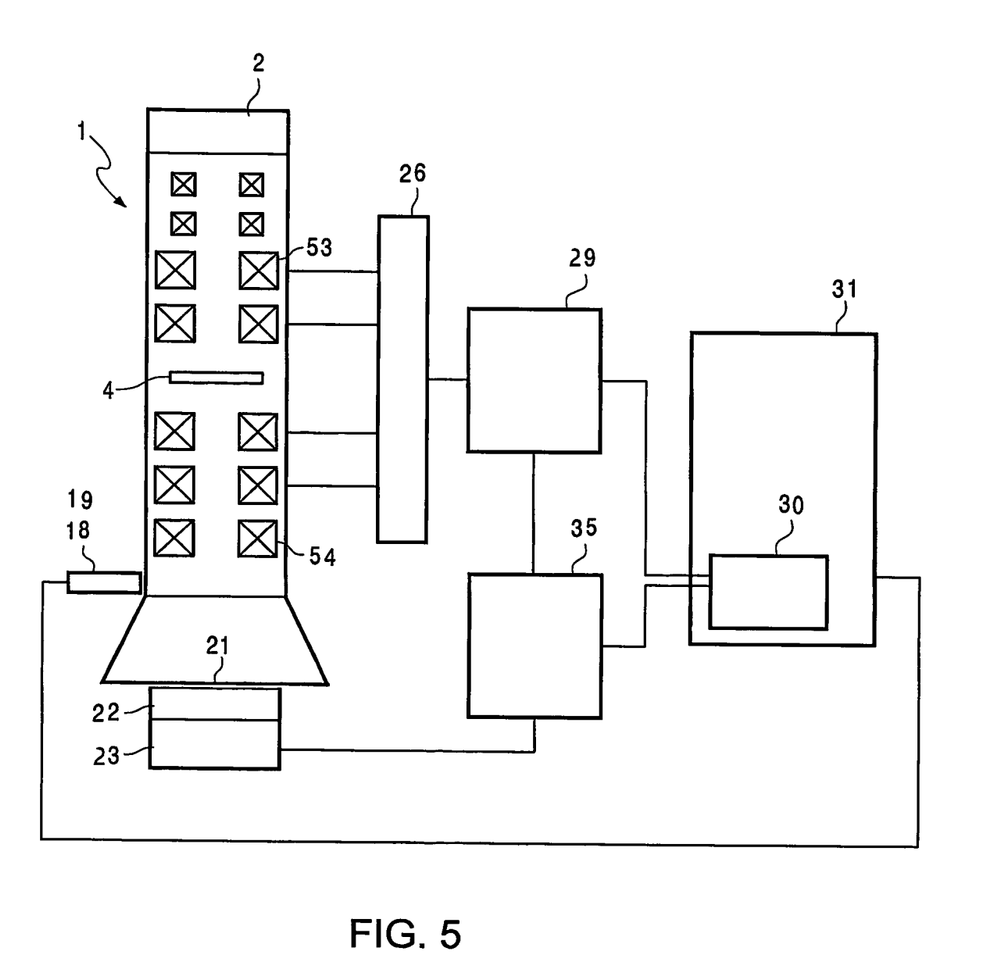

FIG. 5 represents one possible arrangement of one or more devices and a TEM according to the invention. Illustrated is a schematic drawing of a TEM 1 comprising an electron gun 2, deflector coils 53 located before the sample, the sample 4, deflector coils 54 located after the sample and a fluorescent screen 21. Coupled to the TEM are one or more devices according to the invention: a CCD camera 19 or diffractometer 18 which here is positioned into a 35 mm port and is connected to a computer 12, via an analogue to digital (A/D) converter if necessary; a mechanical interface, 22 of the invention to which a Faraday cage, 23 may be coupled; said Faraday cage is connected to an analogue to pre-amplifier and analogue to digital converter 35; the electronic lenses (coils) of the TEM are connected to an electronic rack of amplifiers 26; electronic rack of amplifiers 26, connects to an interface 29 which adjust the signal from the scan generator and precession signal generator located on circuit board 30 such that they are suitable for input into the electronic rack of amplifiers 26. Interface 29 is connected to a scan generator and precession signal generator 30, which in turn is connected to a computer 12; the scan generator and precession signal generator are present in the computer, in this example, as an internal circuit board. The computer has a computer readable media comprising an image of the software described in FIG. 2. In this example, the pre-amplifier/analogue to digital converter 35 is connected to the interface 29.

Figure 6:
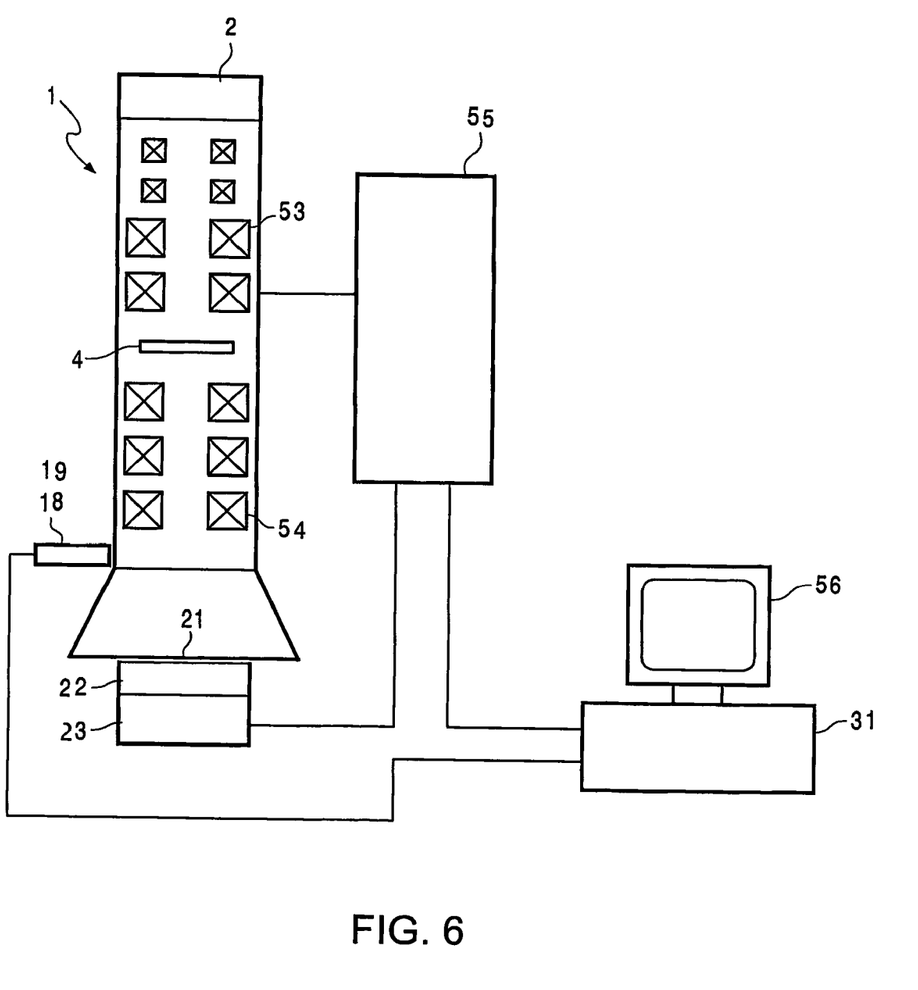

FIG. 6 represents another possible arrangement of one or more devices and a TEM according to the invention. Illustrated is a schematic drawing of a TEM 1 comprising an electron gun 2, deflector coils 53 located before the sample, the sample 4, deflector coils 54 located after the sample and a fluorescent screen 21. A single device 55, connected to the TEM 1, contains a coil pre-amplifier if necessary, an interface, a scan generator, precession signal generator, a preamplifier and analogue to digital converter for connection to the Faraday cage 23. Device 55 is connected to a computer 31, with a computer monitor 56. The computer has a computer readable media comprising an image of the software described in FIG. 2. A CCD camera 19 or diffractometer 18 mounted in a 35 mm port connects to the computer 31 in this example, though it may equally well connect to the device 55, said device containing the necessary circuitry for transfer of data from the CCD camera 19 or diffractometer 18 to the computer 31.

What is claimed is:

1. A method for measuring electron diffraction, ED patterns of a sample, said patterns suitable for structure determination therefrom using a transmission electron microscope, TEM, comprising scanning the ED pattern by means of deflector coils in the TEM situated after the sample, and precessing the electron beam by means of deflector coils in the TEM situated before the sample, in combination with a similar precession of the ED pattern by means of deflector coils situated after the sample.

2. The method according to claim 1, wherein said coils situated after the sample for scanning the ED pattern and precessing the electron beam are the same.

3. The method according to claim 1 further comprising the steps before measurement of intensities of:
   a) exposing said sample to a low electron beam dose,
   b) fast recording an ED pattern using a charged-coupled device, CCD, camera, or, fast recording an ED pattern using a diffractometer in fast scan mode,
   c) blanking the beam,
   d) deducing one or more parameters from the ED pattern obtained in step b) to be used during the measurement of intensities,
   e) de-blanking the beam, and
   f) measuring precise intensities using the parameters determined in step d).

4. The method according to claim 3 wherein parameters of step d) are one or more of:
   the number of spots or areas of the reciprocal space to be scanned,
   number of scanning steps, and
   the step size.

5. The method according to claim 1 further comprising the steps of
   a) comparing the intensity of a particular reflection measured during measurement of intensities with a reference reflection determined by the ED pattern captured by the diffractometer,
   b) determining sample degradation and/or beam stability from the comparison made in step a), and
   c) adjusting any parameters during measurement of intensities and/or adjusting the analysis after measurement of intensities.

6. The method according to claim 1 further comprising the steps of:
   a) measuring the electron beam current during measurement of intensities using an insulated condenser diaphragm located in the path of the beam before the beam contacts the sample,
   b) determining beam stability by monitoring current in step a) over time, and
   c) adjusting any parameters during measurement of intensities and/or adjusting the analysis after measurement of intensities.

7. The method according to claim 1 wherein one or more Faraday cages are used to measure the reflections of the ED pattern during the measurement of intensities.

8. A method according to claim 7 further comprising the following steps:
   a) allowing charge from a Faraday cage to accumulate on a preamplifier which has a few femtoamperes of leakage current; the positive charge from transitive currents engaging said amplifier,
   b) discharging said Faraday cage during measurement of intensities by means of the electron beam,
   c) resolving the work of counter pulses using a managing two-threshold comparator acting from a quartz generator during a cycle of measurement,
   d) determining the charge on the Faraday cage from the output of said amplifier, and
   e) determining the current of an electron beam from the number of pulses which have been recorded in the counter.

9. The method according to claim 1 wherein a combination of a scintillator and a photomultiplier is used to analyse the ED pattern during measurement of intensities.

10. The method according to claim 1 wherein a continuous dynode electron multiplier, CDEM, is used to analyse the ED pattern during measurement of intensities.

11. A device suitable for interfacing with a TEM, enabling said TEM to measure ED patterns of a sample according to the method of claim 1, said patterns suitable for structure determination, comprising a scan generator and a precession signal generator in which the scan generator is configured to scan the ED pattern in x and/or y direction or a spiral mode following the symmetry of the ED pattern and according to the precession protocol.

12. The device according to claim 11 further comprising an inverter and adapter connected to the output of the signal precession generator.

13. The device according to claim 11 further comprising a CCD camera and/or a diffractometer.

14. The device according to claim 11 further comprising an insulated condenser diaphragm located in the path of the beam, before the beam contacts the sample.

15. The device according to any of claim 11 further comprising one or more Faraday cage, a combination of a scintillator and a photomultiplier, and/or a CDEM, each having an analogue-to-digital converting means.

16. The device according to claim 11 further comprising a computer having a computer readable storage means which interfaces to one or more of the above devices.

17. The device according to claim 11 further comprising a mounting enabling one or more Faraday cages, a combination of a scintillator and a photomultiplier, and/or a CDEM to be fitted at the bottom of the TEM column, and/or in the 35 mm camera port, and/or in any available port.

18. The device according to claim 11 further comprising a Faraday cage preamplifier that has a current leakage of between 1 and 50 femtoamperes.

19. A method of structure determination which comprises measuring ED patterns of a sample using the device of claim 11, said patterns suitable for structure determination therefrom using a transmission electron microscope.

20. The method according to claim 1, further comprising a step of determining sample degradation in the sample comprising comparing the intensity of a particular reflection measured during measurement of intensities with a reference reflection determined by the ED pattern captured by the CCD camera or a diffractometer.

21. A TEM comprising a scan generator configured to control coils for scanning an ED pattern, and a precession signal generator configured to control coils that precess an electron beam, said TEM configured to perform a method according to claim 1.

22. A TEM comprising a device according to claim 11.

23. A device suitable for interfacing with a TEM, enabling said TEM to measure ED patterns of a sample, said patterns suitable for structure determination, comprising a precession signal generator and a CCD camera, which camera is configured to set parameters used during the measurement of intensities.

* * * * *

UNITED STATES PATENT AND TRADEMARK OFFICE
CERTIFICATE OF CORRECTION

PATENT NO.       : 7,601,956 B2                               Page 1 of 1
APPLICATION NO.  : 10/570336
DATED            : October 13, 2009
INVENTOR(S)      : Sergeevich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this

Fifth Day of October, 2010

David J. Kappos
*Director of the United States Patent and Trademark Office*